(12) United States Patent
El-Araby et al.

(10) Patent No.: US 11,458,144 B1
(45) Date of Patent: Oct. 4, 2022

(54) METHODS FOR USING 5-HMF ANALOGS WITH INCREASED SOLUBILITY TO INHIBIT OR REVERSE RBC SICKLING

(71) Applicants: King Abdulaziz University, Jeddah (SA); The Children's Hospital of Philadelphia, Philadelphia, PA (US); Virginia Commonwealth University, Richmond, VA (US)

(72) Inventors: Moustafa E. El-Araby, Jeddah (SA); Abdelsatter M. Omar, Jeddah (SA); Osheiza Abdulmalik, Philadelphia, PA (US); Martin K. Safo, Richmond, VA (US)

(73) Assignees: KING ABDULAZIZ UNIVERSITY, Jeddah (SA); THE CHILDREN'S HOSPITAL OF PHILADELPHIA, Philadelphia, PA (US); VIRGINIA COMMONWEALTH UNIVERSITY, Richmond, VA (US)

( * ) Notice: Subject to any disclaimer, the term of this patent is extended or adjusted under 35 U.S.C. 154(b) by 0 days.

(21) Appl. No.: 17/560,795

(22) Filed: Dec. 23, 2021

(51) Int. Cl.
| A61K 31/5377 | (2006.01) |
| A61K 31/341 | (2006.01) |
| A61K 31/4155 | (2006.01) |
| A61P 7/06 | (2006.01) |
| A61K 31/496 | (2006.01) |
| A61K 31/351 | (2006.01) |
| A61K 31/4525 | (2006.01) |

(52) U.S. Cl.
CPC ........ *A61K 31/5377* (2013.01); *A61K 31/341* (2013.01); *A61K 31/351* (2013.01); *A61K 31/4155* (2013.01); *A61K 31/4525* (2013.01); *A61K 31/496* (2013.01); *A61P 7/06* (2018.01)

(58) Field of Classification Search
None
See application file for complete search history.

(56) References Cited

U.S. PATENT DOCUMENTS

| 7,119,208 B2 * | 10/2006 | Safo | C07D 417/04 548/201 |
| 7,160,910 B2 * | 1/2007 | Safo | A61P 7/00 514/448 |
| 10,344,001 B2 * | 7/2019 | Safo | A61P 7/00 |
| 10,836,729 B1 | 11/2020 | Omar et al. | |
| 10,844,022 B1 * | 11/2020 | El-Araby | C07D 307/52 |
| 10,875,834 B2 * | 12/2020 | Safo | C07D 417/04 |
| 11,065,277 B2 * | 7/2021 | Branch | A61K 31/437 |
| 11,104,632 B1 * | 8/2021 | Omar | C07C 47/58 |
| 11,180,458 B2 * | 11/2021 | El-Araby | C07D 405/06 |
| 11,220,485 B2 * | 1/2022 | El-Araby | C07C 237/22 |
| 2013/0018092 A1 | 1/2013 | Stern | |

OTHER PUBLICATIONS

Omar et al., "Aryloxyalkanoic Acids as Non-Covalent Modifiers of the Allosteric Properties of Hemoglobin", 2016, Molecules, 21(8:1057), pp. 1-24. (doi:10.3390/molecules21081057) (Year: 2016).*
Omar et al., "An Investigation of Structure-Activity Relationships of Azolylacryloyl Derivatives Yielded Potent and Long-Acting Hemoglobin Modulators for Reversing Erythrocyte Sickling", 2020, Biomolecules, 10(11:1508), pp. 1-21. (doi:10.3390/biom10111508) (Year: 2020).*
Abdulmalik et al.; "5-hydroxymethyl-2-furfural modifies intracellular sickle haemoglobin and inhibits sickling of red blood cells"; British Journal of Haematology, 2005, vol. 128, pp. 552-561.
Hanneman et al.; "Effects of 5-hydroxymethyl-2-furfural on the volume and membrane permeability of red blood cells from patients with sickle cell disease"; The Journal of Physiology, 2014, vol. 592, No. 18, pp. 4039-4049.
Kassa et al.; "Antisickling Drugs Targeting βCys93 Reduce Iron Oxidation and Oxidative Changes in Sickle Cell Hemoglobin"; Frontiers in Physiology, Jul. 2019, vol. 10, article 931, pp. 1-12.
Oder et al.; "New Developments in Anti-Sickling Agents: Can Drugs Directly Prevent the Polymerization of Sickle Haemoglobin In Vivo?"; British Journal of Haematology, Oct. 2016, vol. 175, No. 1, pp. 24-30.
Okpala et al.; "Investigational agents for sickle cell disease"; 2006, Abstract only.
Safo et al.; "Therapeutic Strategies to Alter Oxygen Affinity of Sickle Hemoglobin"; Hematol Oncol Clin North Am., Apr. 2014, vol. 28, No. 2, pp. 217-231.
Xu et al.; "Design, Synthesis, and Biological Evaluation of Ester and Ether Derivatives of Antisickling Agent 5-HMF for the Treatment of Sickle Cell Disease"; Mol Pharm, Oct. 2, 2017, vol. 14, No. 10, pp. 3499-3511.

* cited by examiner

*Primary Examiner* — My-Chau T. Tran
(74) *Attorney, Agent, or Firm* — WCF IP

(57) ABSTRACT

Methods for administering compounds provide a rapid treatment for sickle cell disease (SCD) to inhibit or reverse red blood cell sickling. The compounds are a group of 5-hydroxymethylfurfural (5-HMF) analogs modified to increase water-solubility. The compounds can be formulated in an aqueous carrier and administered intravenously for immediate uptake into red blood cells (RBCs) within hours, rather than days or weeks. In vitro experiments demonstrated rapid uptake into RBCs and increased $O_2$ affinity of HbS to an equilibrium point within 30 to 90 minutes. The compounds have a desired level of safety as well as a short half-life, both of which are compatible with acute usage. Thus, the methods of treatment rapidly achieve therapeutic steady-state drug levels, making it possible to deliver a treatment in critical emergency care situations to prevent, reverse and otherwise treat acute sickling or anemia.

4 Claims, 5 Drawing Sheets
(4 of 5 Drawing Sheet(s) Filed in Color)

METHODS FOR USING 5-HMF ANALOGS WITH INCREASED SOLUBILITY TO INHIBIT OR REVERSE RBC SICKLING

ACKNOWLEDGEMENT OF SPONSORED RESEARCH

This project was funded by Science and Technology Unit, King Abdulaziz University, Kingdom of Saudi Arabia; Award Number UE-41-110.

BACKGROUND OF THE INVENTION

Field of the Invention

The invention generally relates methods for treating a subject suffering from sickle cell disease. The invention comprises compounds with enhanced solubility for rapid administration to inhibit or reverse sickling of erythrocytes. The invention is particularly useful for treatment in response to an acute or emergency indication of hypoxic sickling.

Background

Sickle cell disease (SCD) is the most common inherited hematologic disorder, affecting over 20-25 million worldwide.[1-3] The pathophysiology of the disease arises as a result of a single point mutation in the β-globin gene that changes βGlu6 of normal Hb (HbA) to βVal6 to form sickle hemoglobin (HbS). Sickle Hb under hypoxia or when deoxygenated polymerizes into long and rigid fibers as a result of a intermolecular contact between the mutated βVal6 of a deoxygenated HbS molecule and a hydrophobic acceptor pocket of an adjacent deoxygenated HbS, causing sickling of red blood cells (RBCs).[4] The rigid RBCs impair blood flow, causing hemolysis and several interrelated adverse effects that include adhesion of RBCs to vascular endothelium, hemolysis of RBC, oxidative stress, inflammation, vaso-occlusion (VOC), and eventually chronic organ damage that eventually leads to poor quality of life and early death.[5-9] In addition to the chronic adverse events, the disease is also characterized by several acute complications or crises that include VOC pain events, chest syndrome, fatigue, and acute life-threatening anemia and stroke. Acute crises require immediate and fast treatment responses, however there are currently no viable drugs to treat such complications.

In recent years, aromatic aldehydes therapy has become an important treatment option for SCD because of the compounds ability to prevent the primary pathophysiology of hypoxia-induced erythrocyte sickling, and the expectedly the downstream secondary adverse effects. The antisickling activity of aromatic aldehydes for the most part depends on their ability to form Schiff-base interaction with the N-terminal αVal1 amines to increase the protein affinity for oxygen since the high-$O_2$ affinity HbS does not sickle. The Schiff-base interaction can be quantified as a Hb-drug adduct (drug-modified Hb), while the change in Hb affinity for oxygen is quantified as a $P_{50}$ shift, which is the partial pressure ($PO_2$) at which 50% of Hb is saturated with oxygen ($SO_2$). These compounds form a reversible Schiff-base adduct with the N-terminal αVal1 amines of the two α-globins and shifts the allosteric equilibrium of Hb from the T-state (low-$O_2$-affinity Hb) to the R-state (high-$O_2$-affinity Hb). The result is an increase concentration of the non-polymer forming oxygenated HbS, which leads to inhibition of RBC sickling.[10-15] Voxelotor (Oxbryta, aka GBT440) is the first such aromatic aldehyde to be approved in 2019 to treat the disease.[16-19] While the long half-life of Voxelotor is beneficial for chronic oral therapy, the terminal half-lives and long time to reach steady state therapeutic drug levels makes Voxelotor unsuitable for urgent treatment. Moreover, Voxelotor is highly hydrophobic with significant solubility problems, which preclude simple parenteral delivery for drug loading for an acute condition. 5-hydroxymethylfurfural (5-HMF) is a natural aromatic aldehyde, which has been studied extensively for its antisickling potential, undergoing various stages of non-clinical studies and clinical trials. Despite improvement in several clinical symptoms, 5-HMF failed to advance for chronic use in treating SCD due in part to low potency and poor oral bioavailability as a result of its short half-life. Nonetheless, a short half-life may be important for drugs treating chronic illness, as they might allow for immediate steady-state therapeutic drug level, as well as allow physicians to be able to reverse drug effects. Unlike Voxelotor, 5-HMF is highly soluble and could potentially be formulated for parental acute use to treat SCD. Targeted modification to the 5-hydroxymethyl moiety into esters and ethers resulted in ~3-fold improvement in antisickling potency of one of the compounds over 5-HMF, as described in U.S. Pat. No. 10,836,729 and by Xu et al.[15] However, 5-HMF was highly insoluble in water and therefore could not be easily formulated for IV dose.

Thus, the most effective treatments currently used to manage SCD are hydrophobic compounds suitable for chronic treatment, but these can take days to weeks to reach a therapeutic level in the blood, making them unsuitable for emergencies, such as the sickling crises that occur with SCD. There is currently no product on the market that meets the criteria physiochemical and PK properties that would allow for intravenous, subcutaneous, or intramuscular loading for acute treatment.

SUMMARY OF THE INVENTION

This invention is a method of use for furfural derivatives or analogs of a compound known as 5-hydroxymethylfurfural (5-HMF). The furfural derivatives or analogs of 5-HMF were found to exert surprisingly much higher antisickling activities than 5-hydroxymethylfurfural but maintain high polar and high solubility properties. These properties make the compounds of the invention suitable for formulations for parenteral use in emergency cases.

In one embodiment, the invention is a method of inhibiting or reversing sickling of red blood cells comprising hemoglobin S (HbS), comprising the steps of contacting red blood cells with a therapeutically effective amount of a furfural derivative or analog having the chemical structure of a compound selected from the group consisting of 5-(difluoromethyl)furan-2-carbaldehyde (MMA-502), 5-(1H-pyrazol-5-yl)furan-2-carbaldehyde (MMA-503), 5-(4-hydroxypiperidin-1-yl)furan-2-carbaldehyde (MMA-504), 5-formylfuran-2-carbonitrile (MMA-505), 5-(4-methylpiperazin-1-yl)furan-2-carbaldehyde; oxalic acid (MMA-506), 5-oxcan-2-yl)furan-2-carbaldehyde (MMA-509), 5-(2,6-dimethymorphlin-4-yl(furan-2-carbaldehyde (MMA-511), and 5-phenoxyfuran-2-carbaldehyde (MMA-512).

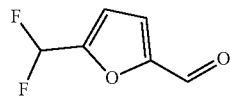

MMA-502

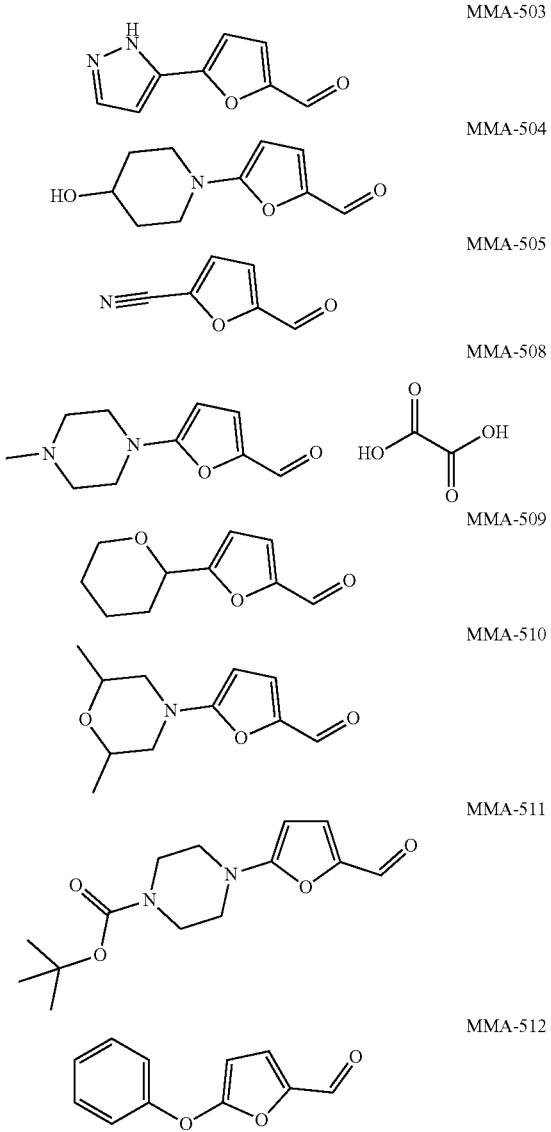

The therapeutically effective amount is a parenteral loading dose sufficient to reach equilibrium of hemoglobin oxygen affinity in the red blood cells and inhibit or reverse polymerization of HbS. In one embodiment, the equilibrium of the hemoglobin oxygen affinity is reached within 30 to 90 minutes. In another embodiment, the equilibrium of the hemoglobin oxygen affinity is reached within 60 minutes or within 30 minutes. Since an objective of the treatment is to reverse or inhibit red blood cell sickling, the hemoglobin targeted to achieve oxygen affinity equilibrium will be HbS.

In another embodiment, the invention is a method of treating a subject suffering from sickle cell disease (SCD). The method comprises the step of administering to the subject a therapeutically effective amount of a pharmaceutical composition comprising a 5-HMF derivative or analog in a pharmaceutically acceptable carrier selected from the group consisting of 5-(difluoromethyl)furan-2-carbaldehyde (MMA-502), 5-(1H-pyrazol-5-yl)furan-2-carbaldehyde (MMA-503), 5-(4-hydroxypiperidin-1-yl)furan-2-carbaldehyde (MMA-504), 5-formylfuran-2-carbonitrile (MMA-505), 5-(4-methylpiperazin-1-yl)furan-2-carbaldehyde; oxalic acid (MMA-508), 5-oxcan-2-yl)furan-2-carbaldehyde (MMA-509), 5-(2,6-dimethymorphlin-4-yl(furan-2-carbaldehyde (MMA-511), and 5-phenoxyfuran-2-carbaldehyde (MMA-512). The method of treatment is useful for relieving or inhibiting at least one symptom of polymerization of hemoglobin S and/or sickling of red blood cells (RBCs). The at least one symptom is selected from the group consisting of impaired blood flow, hemolysis, adhesion of RBCs to vascular endothelium, oxidative stress, inflammation, vaso-occlusion, anemia and chronic organ damage.

In one embodiment, the pharmaceutical composition is administered intravenously, subcutaneously or intramuscularly. The subject may be suffering from an acute condition or crisis caused by SCD. The therapeutically effective amount of a pharmaceutical composition comprising the compound of the invention increases oxygen affinity of hemoglobin within 30 to 90 minutes. In one embodiment, the therapeutically effective amount may increase oxygen affinity of hemoglobin within 60, 50, 40 or even 30 minutes.

In yet another embodiment, the subject suffers from a chronic condition caused by SCD and the compounds may be formulated for oral administration.

Other features and advantages of the present invention will be set forth in the description of invention that follows, and in part will be apparent from the description or may be learned by practice of the invention. The invention will be realized and attained by the compositions and methods particularly pointed out in the written description and claims hereof.

BRIEF DESCRIPTION OF THE DRAWINGS

The patent or application file contains at least one drawing executed in color. Copies of this patent or patent application publication with color drawings will be provided by the Office upon request and payment of the necessary fee.

The accompanying drawings, which are incorporated in and constitute a part of this specification, illustrate embodiments of the invention and, together with a general description of the invention given above, and the detailed description given below, serve to explain the invention.

DETAILED DESCRIPTION

Figure 1:
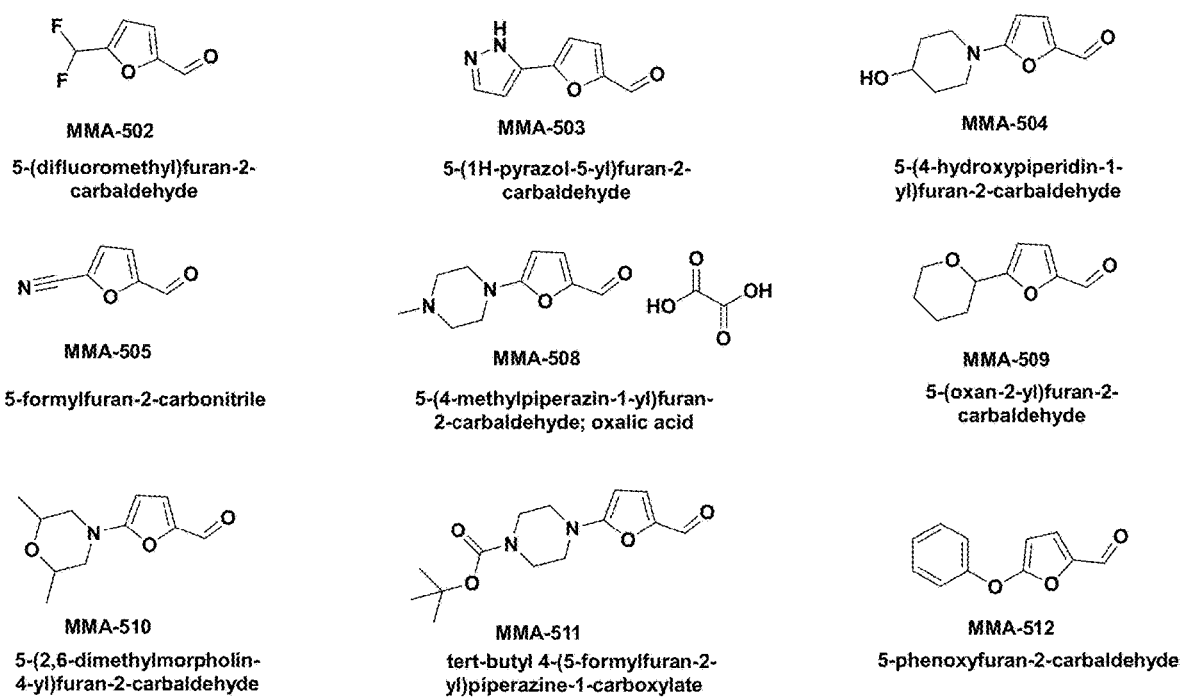
FIG. 1 shows MMA compounds that are analogs of the antisickling agent 5-HMF with increased solubility compared to 5-HMF. The MMA compounds have chemical structures and identification names in parentheses as follows: 5-(difluoromethyl)furan-2-carbaldehyde (MMA-502), 5-(1H-pyrazol-5-yl)furan-2-carbaldehyde (MMA-503), 5-(4-hydroxypiperidin-1-yl)furan-2-carbaldehyde (MMA-504), 5-formylfuran-2-carbonitrile (MMA-505), 5-(4-methylpiperazin-1-yl)furan-2-carbaldehyde; oxalic acid (MMA-508), 5-oxcan-2-yl)furan-2-carbaldehyde (MMA-509), 5-(2,6-dimethymorphlin-4-yl(furan-2-carbaldehyde (MMA-511), and 5-phenoxyfuran-2-carbaldehyde (MMA-512).

The invention comprises furfural derivatives that were surprisingly found to exert much higher antisickling activities than 5-hydroxymethylfurfural but maintain high polar and high solubility properties making them well-suited for parenteral use in emergency cases. The non-toxic nature of the 5-HMF pharmacophore and positive pharmacologic outcome of analogs and derivatives of 5-HMF are combined with an increased potency and physiochemical and PK properties that allow intravenous, subcutaneous, or intramuscular loading for acute treatment. Crystallographic study of 5-HMF and these analogs suggested the importance of hydrogen-bond interactions for binding and potency of these compounds.[10,11,15] Several soluble analogs of 5-HMF that were anticipated to make hydrogen-bond interactions with the protein residues Ser131 and/or Ser138 were identified. The compounds, termed MMA, were tested with 5-HMF as a positive control for their in vitro functional and biological effects, including absorption, distribution, metabolism and excretion (ADME) properties, as well as their mode of interaction with Hb.

As used herein, the terms "furfural derivatives", "furfural analogs", "5-HMF analogs", and various other constructions are used to refer to the compounds of the invention, which are also identified herein as "MMA" or "MMA compounds".

As used herein, the terms "red blood cells", "RBCs" and "erythrocytes" are used interchangeably to refer to the cells of the blood that carry hemoglobin.

As used herein, the term "hemoglobin" is used interchangeably with the abbreviations "Hb" or "Hgb". Hemoglobin can refer to any type, including hemoglobin A (HbA), which comprises subunit alpha 1 (α1) and alpha 2 (α2) and a subunit beta (β) in human adults, and HbA$_2$, HbF, or any other variant. The invention is particularly directed to a treatment for subjects having the variant form of hemoglobin found in sickle cell disease, which is known as hemoglobin S (α$_2$β$^s_2$) and is indicated by the abbreviation HbS throughout the Description and Examples of the invention.

In one embodiment, the invention is a method of inhibiting or reversing sickling of red blood cells (RBCs) comprising hemoglobin S (HbS). The method preserves and/or restores flexibility of RBCs and averts pathological effects of sickling, including impaired blood flow, hemolysis, adhesion of RBCs to vascular endothelium, oxidative stress, inflammation, vaso-occlusion (VOC), and eventually chronic organ damage due to the cumulative effects of repeated episodes of sickling. The method includes a step of contacting red blood cells with a therapeutically effective amount of a furfural derivative or analog, having the chemical structure of a compound selected from the group consisting of 5-(difluoromethyl)furan-2-carbaldehyde (MMA-502), 5-(1H-pyrazol-5-yl)furan-2-carbaldehyde (MMA-503), 5-(4-hydroxypiperidin-1-yl)furan-2-carbaldehyde (MMA-504), 5-formylfuran-2-carbonitrile (MMA-505), 5-(4-methylpiperazin-1-yl)furan-2-carbaldehyde; oxalic acid (MMA-508), 5-oxcan-2-yl)furan-2-carbaldehyde (MMA-509), 5-(2,6-dimethymorphlin-4-yl(furan-2-carbaldehyde (MMA-511), and 5-phenoxyfuran-2-carbaldehyde (MMA-512). Chemical structures for the MMA compounds are:

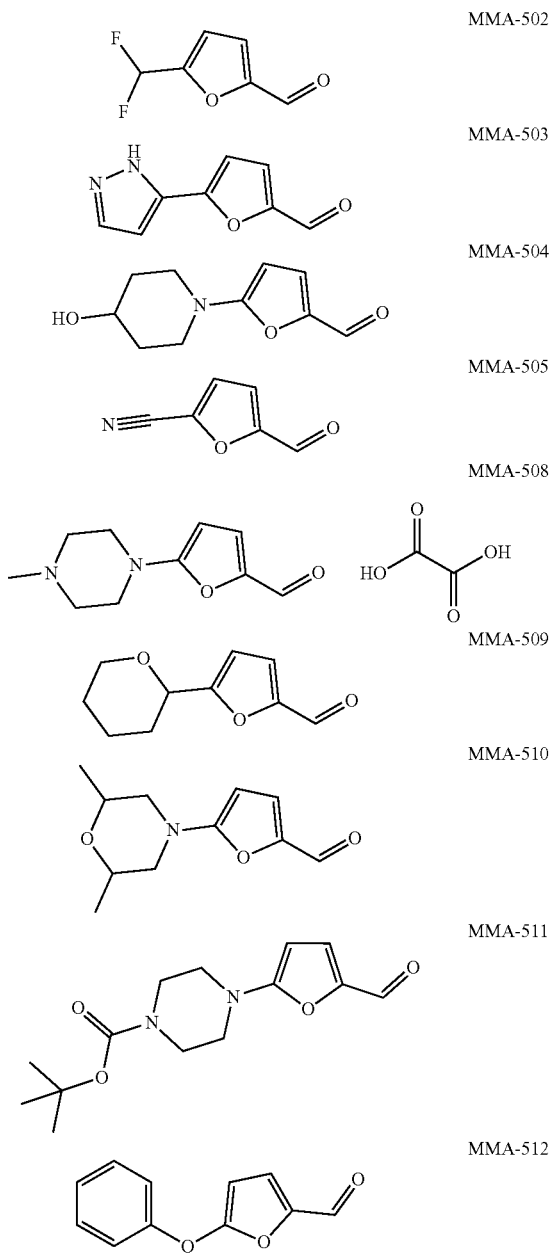

The therapeutically effective amount is a parenteral loading dose sufficient to reach equilibrium of hemoglobin oxygen affinity in the red blood cells and inhibit or reverse polymerization of HbS. In one embodiment, the equilibrium of the hemoglobin oxygen affinity is reached within 30 to 90 minutes. In another embodiment, the equilibrium of the hemoglobin oxygen affinity is reached within 60 minutes or within 30 minutes, making the method of treatment particularly well-suited for an emergency care situation. Since an objective of the treatment is to reverse or inhibit red blood cell sickling, the hemoglobin targeted to achieve oxygen affinity equilibrium will be HbS. In one embodiment, the compound is 5-oxcan-2-yl)furan-2-carbaldehyde, also known herein as MMA-509. In another embodiment, the compound is 5-(1H-pyrazol-5-yl)furan-2-carbaldehyde, also known herein as MMA-503.

Acute crises require immediate and fast treatment responses to prevent or reverse sickling that occurs with SCD. In another embodiment, the invention is a method of treating a subject suffering from SCD. The method comprises the step of administering to the subject a therapeutically effective amount of a pharmaceutical composition comprising a 5-HMF derivative or analog in a pharmaceutically acceptable carrier selected from the group consisting of 5-(difluoromethyl)furan-2-carbaldehyde (MMA-502), 5-(1H-pyrazol-5-yl)furan-2-carbaldehyde (MMA-503), 5-(4-hydroxypiperidin-1-yl)furan-2-carbaldehyde (MMA-504), 5-formylfuran-2-carbonitrile (MMA-505), 5-(4-methylpiperazin-1-yl)furan-2-carbaldehyde; oxalic acid (MMA-508), 5-oxcan-2-yl)furan-2-carbaldehyde (MMA-509), 5-(2, 6-dimethymorphlin-4-yl(furan-2-carbaldehyde (MMA-511), and 5-phenoxyfuran-2-carbaldehyde (MMA-512). The method of treatment is useful for relieving or inhibiting at least one symptom of polymerization of hemoglobin S and/or sickling of red blood cells (RBCs). The at least one symptom is selected from the group consisting of impaired blood flow, hemolysis, adhesion of RBCs to vascular endothelium, oxidative stress, inflammation, vaso-occlusion, anemia, chronic organ damage, VOC pain events, chest syndrome, fatigue, and acute life-threatening anemia and stroke.

In one embodiment, the compound is 5-oxcan-2-yl)furan-2-carbaldehyde, also known herein as MMA-509, having the chemical structure of:

MMA-509

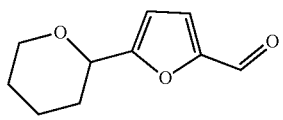

In another embodiment, the compound is 5-(1H-pyrazol-5-yl)furan-2-carbaldehyde, known herein as MMA-503, having the chemical structure of:

MMA-503

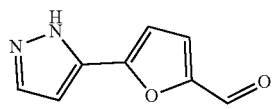

While some MMA compounds were found to have weaker activity in the Examples of the invention, the compounds nonetheless have an enhanced solubility in an aqueous carrier and a short half-life that makes them suitable for use with the method of the invention. Thus, in yet another embodiment, the compound is 5-formylfuran-2-carbonitrile, known herein as MMA-505, having the chemical structure of

MMA-505

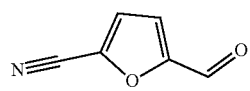

In one embodiment, the pharmaceutical composition is administered parenterally. In other embodiments, it is administered intravenously, subcutaneously or intramuscularly. The subject may be suffering from an acute condition or crisis caused by SCD and is therefore in need of a rapid treatment to provide relief. The therapeutically effective amount of a pharmaceutical composition comprising the compound of the invention increases oxygen affinity of hemoglobin within 30 to 90 minutes. Depending on the identity of the compound, the concentration of the dose, and the route of administration, the therapeutically effective amount may increase oxygen affinity of hemoglobin within 60 minutes. In one embodiment, the therapeutically effective amount may increase oxygen affinity of hemoglobin within 60, 50, 40 or 30 minutes or less.

In yet another embodiment, the subject suffers from a chronic condition caused by SCD. The compounds may be administered parenterally as a loading dose, followed by a formulation suitable for oral administration. The properties of rapid time to oxygen affinity equilibration and a short half-life make the oral formulation suitable for chronic administration.

The compounds of the disclosure may form salts which are also within the scope of this disclosure. Pharmaceutically acceptable (i.e., non-toxic, physiologically acceptable) salts are preferred, although other salts are also useful, e.g., in isolating or purifying the compounds of this disclosure.

"Salts" or "pharmaceutically acceptable salts" refers to the relatively non-toxic, inorganic and organic acid addition salts, and base addition salts, of compounds of the present disclosure. These salts can be prepared in situ during the final isolation and purification of the compounds. In particular, acid addition salts can be prepared by separately reacting the purified compound in its free base form with a suitable organic or inorganic acid and isolating the salt thus formed.

Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulfamates, malonates, salicylates, propionates, methylene-bis-.beta.-hydroxynaphthoates, gentisates, isethionates, di-p-toluoyltartrates, methanesulfonates, ethanesulfonates, benzenesulfonates, p-toluenesulfonates, cyclohexylsulfamates and laurylsulfonate salts, and the like. See, for example S. M. Berge, et al., "Pharmaceutical Salts," J. Pharm. Sci., 66, 1-19 (1977) which is incorporated herein by reference. Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide and the like. Suitable amine base addition salts are prepared from amines which have sufficient basicity to form a stable salt, and preferably include those amines which are frequently used in medicinal chemistry because of their low toxicity and acceptability for medical use such as ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like A solvate is the result of solvation which is an interaction of a solute (i.e., a compound of the disclosure) with a solvent. Solvation leads to stabilization of the solute species in the solution. A solvate refers to the solvated state, whereby an ion in a solution is surrounded or complexed by solvent molecules. Exemplary solvents include, but are not limited to, propylene glycol; polypropylene glycol; polyethylene glycol (for example, polyethylene glycol 300, polyethylene glycol 400, polyethylene glycol 600, polyethylene glycol 900, polyethylene glycol 540 (all available from Union Carbide) and the like); pharmaceutically acceptable alcohols (for example, ethanol or 2-(2-ethoxyethoxy)ethanol (Transcutol®, Gattefosse, Westwood, N.J. 07675) and the like); polyoxyethylene castor oil derivatives (for example, polyoxyethyleneglycerol triricinoleate or polyoxyl 35 castor oil (Cremophor®EL, BASF Corp.), polyoxyethyleneglycerol oxystearate (Cremophor®RH 40 (polyethyleneglycol 40 hydrogenated castor oil) or Cremophor®RH 60 (polyethyleneglycol 60 hydrogenated castor oil), BASF Corp.) and the like); fractionated coconut oil (for example, mixed triglycerides with caprylic acid and capric acid (Miglyol®812, available from Huls AG, Witten, Germany) and the like); Tween®80; isopropyl palmitate; isopropyl myristate; pharmaceutically acceptable silicon fluids; and the like.

The compound may be combined with pharmaceutically acceptable excipients. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The compounds described herein are useful for the treatment of diseases that can be ameliorated by increasing Hb oxygen affinity, for example, SCD (which may also be referred to as "sickle cell anemia"), and hypoxia-underlying or associated diseases, e.g. hemorrhagic and traumatic shock, cardiac arrest and cardiogenic shock, traumatic brain injury, cancer, stroke, myocardial infarction, myocardial ischemia, vaso-occlusive crisis, etc. The treatment methods disclosed herein may include a step of diagnosing a subject with SCD or hypoxia-underlying diseases, e.g. hemorrhagic and traumatic shock, cardiac arrest and cardiogenic shock, traumatic brain injury, cancer, stroke, myocardial infarction, myocardial ischemia, vaso-occlusive crisis, etc. The compounds described herein can also be used to increase tissue oxygenation or as a means to hyperoxygenate tumors making them more susceptible to radiation therapy.

Exemplary methods of the invention can be used to treat any patient or subject suffering from or likely to suffer from a disease or condition which can be prevented, treated, cured, or ameliorated (i.e., disease symptoms are abated) by increasing oxygenation to hypoxic tissues. Various embodiments or scenarios of use of the methods of the invention include but are not limited to patients who have incurred an acute or chronic illness or injury in which the body has become hypoxic. The agents act to enhance oxygen delivery from hemoglobin to the hypoxic tissue.

The exemplary methods of the invention involve administering compositions comprising at least one (i.e., one or more) of the compounds disclosed herein to a patient in need thereof. The present disclosure thus also provides compositions which comprise the compounds as described herein, usually together with a pharmacologically suitable carrier or diluent. In some embodiments, one substantially purified compound is present in a composition; in other embodiments more than one compound is present, each compound being substantially purified prior to being mixed in the composition. The preparation of pharmacologically suitable compositions for use as medicaments is well known to those of skill in the art. Typically, such compositions are prepared either as liquid solutions or suspensions, however solid dry forms such as tablets, pills, powders and the like are also contemplated. The liquid may be an aqueous liquid. Solid forms suitable for solution in, or suspension in, liquids prior to administration may also be prepared. The preparation may also be emulsified. The active ingredients may be mixed with excipients which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. If it is desired to administer an oral form of the composition, various thickeners, flavorings, diluents, emulsifiers, dispersing aids or binders and the like may be added. The composition of the present disclosure may contain any such additional ingredients so as to provide the composition in a form suitable for administration. The final amount of compound in the formulations may vary. However, in general, the amount in the formulations will be from about 1% to about 99%.

The compound compositions (preparations) of the present disclosure may be administered by any of the many suitable means which are well known to those of skill in the art, including but not limited to: by injection, inhalation, orally, intravaginally, intranasally, by ingestion of a food or product containing the compound, topically, as eye drops, via sprays, etc. In exemplary embodiments, the mode of administration is by injection or orally. In addition, the compositions may be administered in conjunction with other treatment modalities which are used to treat SCD or other conditions associated with hypoxia, examples of which include but are not limited to the administration of hydroxyurea, L-glutamine (Endari), Crizanlizumab (Adakveo), Voxelotor (Oxbryta, aka GBT440), vanillin, supplemental oxygen, allosteric effectors of Hb, including other agents that increase the oxygen affinity of hemoglobin, e.g. 5-HMF, agents that decrease Hb affinity for oxygen, e.g. RSR13, etc.

The compositions of the present disclosure may also contain other components such as, but not limited to, additives, adjuvants, buffers, tonicity agents, and preservatives. In any of the compositions of this disclosure, the mixtures are preferably formulated at about pH 5 to about pH 8. This pH range may be achieved by the addition of buffers to the composition. It should be appreciated that the compositions of the present disclosure may be buffered by any common buffer system such as phosphate, borate, acetate, citrate, carbonate and borate-polyol complexes, with the pH and osmolality adjusted in accordance with well-known techniques to proper physiological values.

Embodiments of the disclosure also include methods of preparing the compounds and compositions disclosed herein. Various suitable methods are known in the art. A patient or subject to be treated by any of the compositions or methods of the present disclosure can mean either a human or a non-human animal including, but not limited to dogs, horses, cats, rabbits, gerbils, hamsters, rodents, birds, aquatic mammals, cattle, pigs, camelids, and other zoological animals.

In some embodiments, the compound is administered to the subject in a therapeutically effective amount. By a "therapeutically effective amount" is meant a sufficient amount of active agent to treat the disease or disorder at a reasonable benefit/risk ratio applicable to any medical treatment. It will be understood that the total daily usage of the compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific active agent employed; and like factors well known in the medical arts. For example, it is well within the skill of the art to start doses of the compound at levels or frequencies lower than those required to achieve the desired therapeutic effect and to gradually increase the dosage or frequency until the desired effect is achieved. However, the daily dosage of the active agent may be varied over a wide range from 0.01 to 1,000 mg per adult per day. In particular, the compositions contain 0.01, 0.05, 0.1, 0.5, 1, 5, 10, 20, 30, 40, 50, 60, 70, 80, 90, 100, 150, 200, 250, 300, 350, 400, 450, 500, 550, 600, 650, 700, 750, 800, 850, 900, 950, or 1000 mg of the compound, including all multiples of 5 and 10 between 0.01 and 1000 (e.g. 100, 105, 110, 115, etc.). An effective amount of the drug is ordinarily supplied at a dosage level from 0.0002 mg/kg to about 20 mg/kg of body weight per day, especially from about 0.001 mg/kg to 7 mg/kg of body weight per day.

The following descriptions and examples illustrate some exemplary embodiments of the disclosed invention in detail. Those of the skill in the art will recognize that there are numerous variations and modifications of this invention that are encompassed by its scope. Accordingly, the description of a certain exemplary embodiment should not be deemed to limit the scope of the present invention.

Before exemplary embodiments of the present invention are described in greater detail, it is to be understood that this invention is not limited to any particular embodiments described herein and may vary. It is also to be understood that the terminology used herein is for the purpose of describing particular embodiments only, and is not intended to be limiting, since the scope of the present invention will be limited only by the appended claims.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

EXAMPLES

The following Examples provide exemplary compositions and methods for practicing the invention. The Examples employ the following Materials and Methods for embodiments illustrated in FIGS. 1-5. Additional details can be found in the section entitled "Brief Description of the Drawings".

General Procedures

MMA compounds with improved solubility were purchased from Molport (Riga, Latvia), with chemical names and structures shown in FIG. 1. All compounds, including the positive control 5-HMF were solubilized in DMSO and used for the tests as indicated for each Example. The corresponding control experiments (without test compound) also contain DMSO. Normal whole blood was collected from adult donors (>18 years) after informed consent, in accordance with regulations of the IRB for Protection of Human Subjects (IRB #HM1) by the VCU Human Research Protection Program/Institutional Review Board. Leftover blood samples from patients with homozygous SS were obtained and utilized, based on an approved IRB protocol (IRB #11-008151) by the Committees for the Protection of Human Subjects of the Institutional review board at the Children's Hospital of Philadelphia. All experimental protocols and methods were performed in accordance with institutional (VCU and CHOP) regulations. Purified human adult Hb in 50 mM Bis Tris buffer, pH 6.8, was prepared from discarded human blood as previously described[10] and stored at −80° C. until ready for crystallization.

Example 1—HB Adduct Formation, Effect on HB Affinity for Oxygen and Antisickling Activities The effect of the MMA compounds and positive control 5-HMF on RBC sickling, Hb modification, and Hb oxygen equilibrium was studied utilizing SS blood following previous procedure.[27]

For the antisickling study, SS blood (hematocrit 20%) were incubated under air in the absence or presence of all the MMA compounds (0.5 mM, 1 mM and 2 mM) at 37° C. for 1 h, followed by incubating the mixture under hypoxic conditions (2.5% $O_2$) at 37° C. for 2 h. Aliquots with fixed 2% glutaraldehyde solution and under anaerobic condition were subjected to microscopic morphological analysis.[11]

For the oxygen equilibrium study, about 100 μL aliquot of clarified lysate of residual samples from the above antisickling study was added to 4 mL of 0.1 M potassium phosphate buffer, pH 7.0, in cuvettes and subjected to hemoximetry analysis using Hemox™ Analyzer (TCS Scientific Corp., New Hope, Pa.) to assess $P_{50}$ shift, which is the partial pressure of oxygen ($PO_2$) at which 50% of Hb is saturated with oxygen ($SO_2$). Degree of Hb $O_2$ affinity shift ($\Delta P_{50}$) was expressed as percentage fractions of control DMSO-treated samples.

The Hb adduct formation study also used clarified lysates that were subjected to a cation-exchange HPLC (Hitachi D-7000 Series, Hitachi Instruments, Inc., San Jose, Calif.), and a weak cation-exchange column (Poly CAT A: 30 mm×4.6 mm, Poly LC, Inc., Columbia, Md.).

Results

Using homozygous sickle (SS) blood from patients, the MMA compounds (MMA502, MMA503, MMA504, MMA505, and MMA509 were tested with 5-HMF as control for Hb adduct formation, effect on Hb affinity for oxygen and corresponding antisickling activities (RBC morphology study) using previously published protocols.[14,15]

The results as shown in Tables 1-3 suggest varying potencies of the compounds, which were mostly dose-dependent and correlate linearly with each other.

TABLE 1

Sickling inhibition in SS RBCs treated with MMA compounds.

| | % Sickling inhibition | | |
|---|---|---|---|
| Compound | 0.5 mM | 1 mM | 2 mM |
| 502 | 26.2 ± 0.5 | 46.0 ± 2.8 | 48.1 ± 0.4 |
| 503 | 15.4 ± 4.1 | 28.0 ± 13.1 | 69.7 ± 5.5 |
| 504 | 14.6 ± 7.6 | 18.1 ± 2.7 | 21.7 ± 0.3 |
| 505 | 16.3 ± 5.5 | 12.5 ± 0.5 | 47.5 ± 7.5 |
| 509 | 21.6 ± 14.3 | 55.0 ± 3.3 | 81.9 ± 4.4 |
| 5HMF | N/A | N/A | 21.4 ± 0.0 |

TABLE 2

Hb-$O_2$ affinity of SS RBCs treated with MMA compounds.

| | % Hb-$O_2$ affinity | | |
|---|---|---|---|
| Compound | 0.5 mM | 1 mM | 2 mM |
| 502 | 14.2 ± 3.4 | 8.8 ± 0.5 | 31.5 ± 12.7 |
| 503 | 8.0 ± 1.1 | 20.0 ± 2.5 | 37.1 ± 2.5 |
| 504 | 4.4 ± 5.1 | 5.3 ± 1.5 | 2.7 ± 1.2 |
| 505 | 5.5 ± 1.2 | 14.6 ± 2.1 | 32.0 ± 3.0 |
| 509 | 16.3 ± 1.5 | 34.5 ± 14.4 | 58.5 ± 15.3 |
| 5HMF | N/A | N/A | 27.2 ± 4.9 |

TABLE 3

Hb-modification in SS RBCs treated with MMA compounds.

| | % Hb-modification | | |
|---|---|---|---|
| Compound | 0.5 mM | 1 mM | 2 mM |
| 502 | 9.6 ± 0.0 | 20.4 ± 6.6 | 42.4 ± 10.9 |
| 503 | 4.8 ± 2.1 | 18.0 ± 7.9 | 34.6 ± 7.1 |
| 504 | 0.0 ± 0.0 | 0.0 ± 1.0 | 0.4 ± 0.8 |
| 505 | 4.2 ± 1.6 | 10.4 ± 2.6 | 26.7 ± 6.0 |
| 509 | 16.2 ± 0.0 | 27.6 ± 3.6 | 53.3 ± 3.9 |
| 5HMF | N/A | N/A | 33.8 ± 11.7 |

Expectedly, all four compounds MMA509, MMA503, MMA505 and MMA502 also showed significant Hb adduct formation, which at 2 mM were 53%, 35%, 27% and 42%, respectively. These compare with 33% observed for 5-HMF. MMA504 showed the least potent effect, inhibiting sickling by 27%, increasing Hb oxygen affinity by 3%, and almost showing no adduct formation (<1%). Without being bound by theory, the discordant results between the antisickling activity and the other two pharmacodynamic (PD) effects with MMA504 may likely be due to the compounds having additional mechanism of antisickling effect that does not involve Schiff-base formation and/or probably oxygen independent. We have previously studied aromatic aldehydes that show both $O_2$-dependent and $O_2$-dependent antisickling effects, the latter due to direct polymer destabilization by perturbing a surface-located F helix on the α-subunits.[20,21]

Figure 2A:
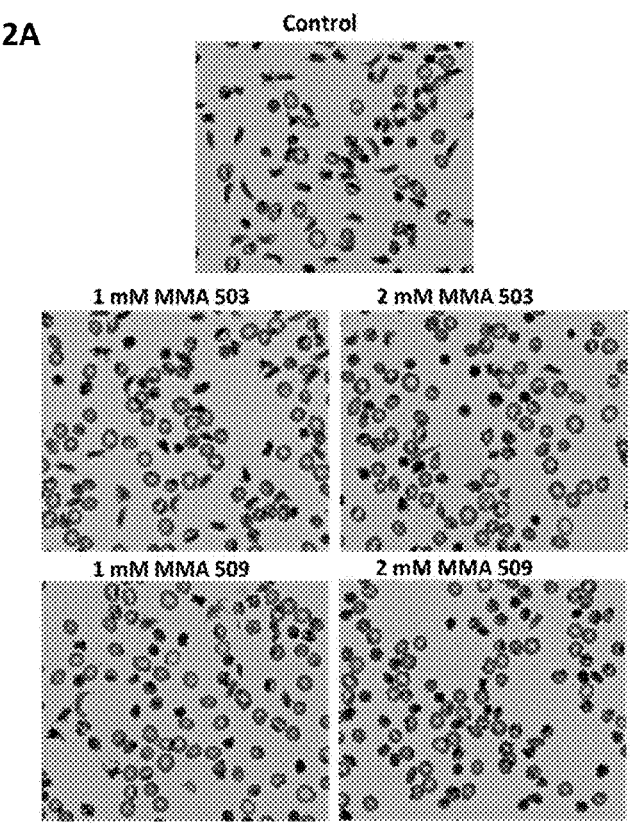
FIGS. 2A and 2B show dose-dependent effects of representative MMA compounds on sickling of SS cells and Hb $O_2$-affinity in vitro (Hct of 20%). (2A) Morphology of SS cells before and after incubation with MMA503 or MMA509 under 2.5% $O_2$. (2B) Representative OEC curves of lysates from the antisickling study of MMA503 or MMA509.
Figure 2B:
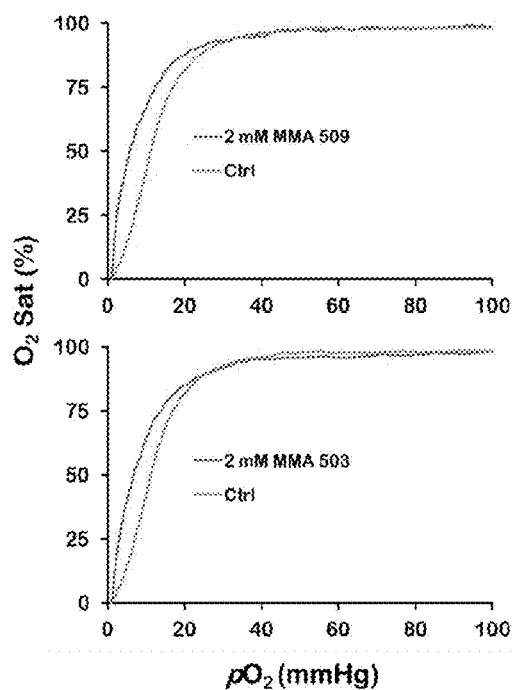
Figure 3:
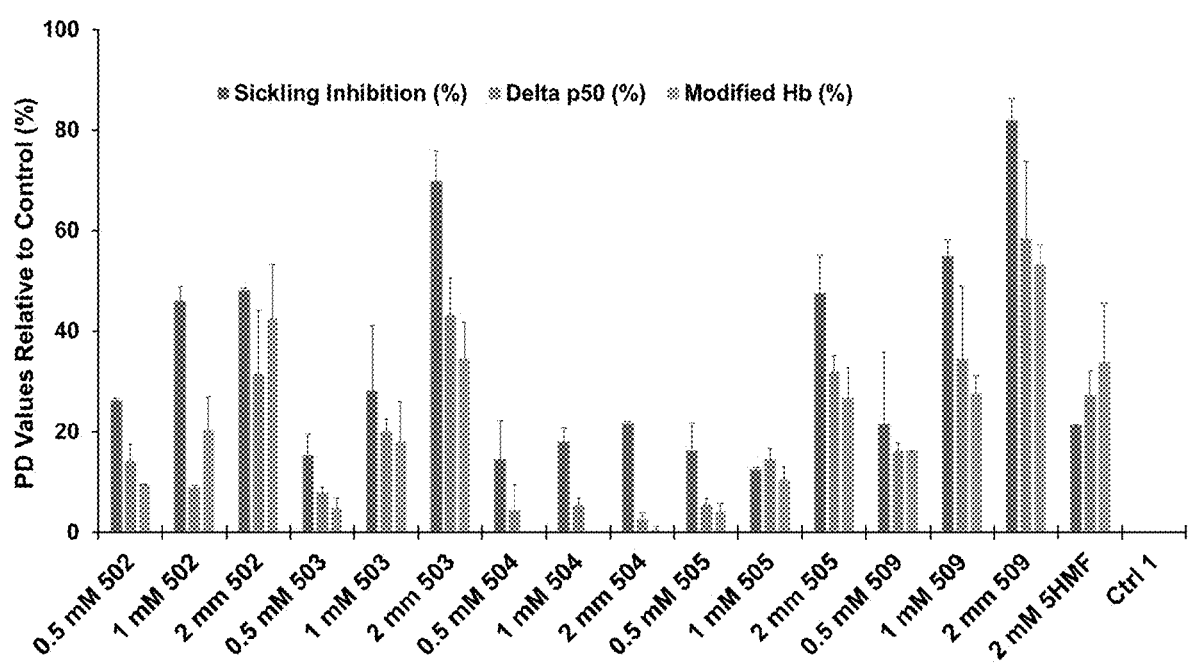
FIG. 3 shows concentration-dependent RBC sickling inhibition, $P_{50}$ shift, and Hb modification (adduct formation) by MMA compounds in SS blood.

In the comparative study of sickling inhibition, the positive control 5-HMF only inhibited RBC sickling by 21% and shifted the $P_{50}$ by 27%, as shown in FIGS. 2A and 2B, clearly suggesting a 3.5-fold to 4.0-fold improvement in antisickling activity. MMA503 and MMA509 at 2 mM concentration showed the most potent effect in increasing Hb oxygen affinity, shifting $P_{50}$ by 37% and 59% with concomitant sickling inhibitions of 70% and 82%, respectively, as shown in FIGS. 2B and 2A. The two compounds MMA502 and MMA505 also potently increased Hb affinity for oxygen ($P_{50}$ of 32% or 40%) and prevented RBC sickling (48% or 55%), the latter ~2.5-fold over 5-HMF, shown in FIG. 3.

Example 2—X-ray Structure of HB in Complex with MMA Compounds

X-ray crystallography was used to determine the mode of interactions between Hb and the MMA compounds following previously published methods[15]. Briefly, the compounds were incubated with 30 mg/dL of CO-ligated Hb in 10:1 molar ratio and crystallized using 10-20% PEG6000, 100 mM Hepes, pH 7.4. X-ray quality crystals were obtained for only MMA509, MMA505, and MMA503, with each single compound in complex with liganded Hb. Diffraction data from the ensuing crystals were collected at 100 K using Rigaku MicroMax™ 007HF X-ray Generator, Eiger R 4M Detector and Oxford Cobra Cryo-system (The Woodlands, Tex.). The crystals were first cryoprotected with 80 μL mother liquor mixed with 62 μL of 50% PEG6000. The diffraction data was processed using d*trek software (Rigaku) and the CCP4 suite of programs. The crystal structures were refined using the Phenix program, with the native isomorphous R2-state crystal structure (PDB ID 1BBB) as a starting model. Model building and correction was carried out using COOT[29-31].

Results

The primary interaction between aromatic aldehydes and Hb involves a Schiff-base interaction between the aldehyde moiety and the N-terminal amine group of α Val1. The stability of the Schiff-base interaction, which obviously impacts the pharmacologic effect of these compounds depends on additional interactions between the bound aromatic aldehydes and the α-cleft residues, including both hydrogen-bond and hydrophobic interactions.[10,11,15] 5-HMF binds to Hb and makes Schiff-base interaction with the αVal1 amines, as well as hydrogen-bond interactions with the hydroxyl of αSer131, αSer134 and αSer138 that stabilize the liganded R state Hb conformation relative to the T state Hb conformation.[10] Like 5-HMF, we anticipated all the MMA compounds to make hydrogen-bond interactions with the serine residues, but unlike 5-HMF we also expected some of the compounds to further make hydrophobic interactions with the protein. We therefore determined the crystal structures of MMA509, MMA503 and MMA505, not only to gain insight into their mechanism of antisickling activity but also help explain their differing potencies. The co-crystallization experiment was conducted as previously described.[13-15] Like 5-HMF and as expected, all three complexes bind two molecules of the respective MMA compounds to the two α-subunits of R2 state Hb, forming Schiff-base adducts with the αVal1 amines of the α1- and α2-subunits.

Figure 4A:
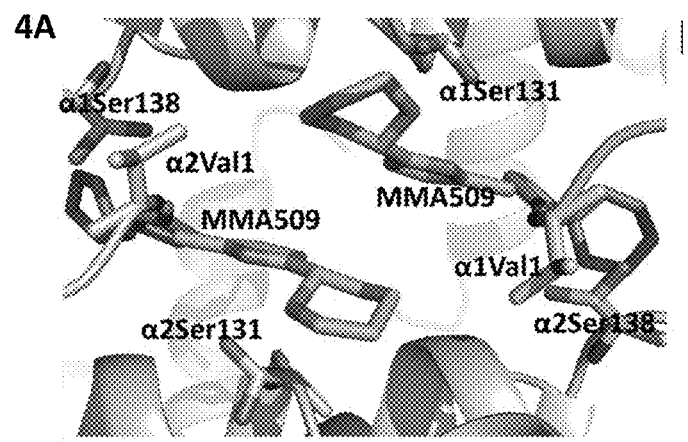
FIGS. 4A-4C show crystal structures of COHb in complex with MMA compounds at the α-cleft of the COHb. The α- and β-subunits are shown in grey and yellow ribbons, respectively, while the bound MMA compounds, as well as the Hb residues Val1, Ser131 and Ser138 are shown in sticks. (4A) Bound MMA-509 in two alternate conformations in cyan and magenta. (4B) Bound MMA-503 in magenta. (4C) Bound MMA-505 in green. Only the α2-subunit bound compound was resolved.
Figure 4B:
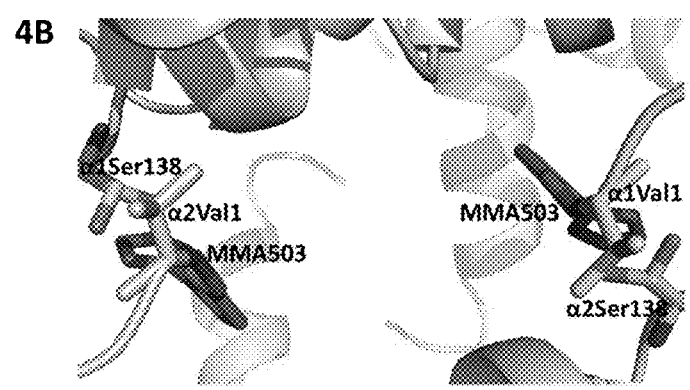
Figure 4C:
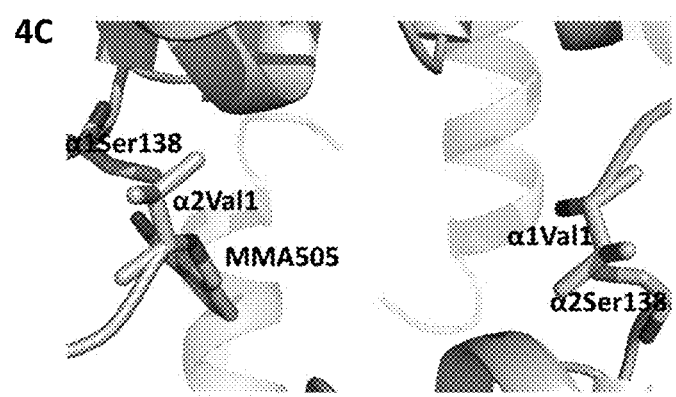

Interestingly, the most potent biological compound MMA509 binds in two alternate conformations at each α-subunit in approximate ratio of 70% and 30% to maximize interactions with the protein (FIG. 4A). This is unlike most aromatic aldehydes, e.g. 5-HMF, or MMA-503 or MMA-505 (see below; FIG. 4B and 4C) that bind in one conformation at each α-subunit. At the α2-subunit where the electron density of the bound MMA-509 is stronger and better defined, the first alternate conformer, in addition to the Schiff-base interaction with αVal1 nitrogen, makes intra-subunit hydrogen-bond interactions that involve its pyranose and furan oxygen atoms with the hydroxyl of α2Ser131. The sidechain of α2Ser131 assumes two alternate conformations to make these two interactions. The pyranose ring of MMA509 also makes hydrophobic interactions with α2Val135, α2Pro77 and α2Met76. The second MMA-509 alternate conformer at the α2-subunit, which is rotated ~180° from the first conformer (FIG. 4A), also in addition to the Schiff-base interaction with α2Val1 nitrogen, makes hydrogen-bond interaction with the protein that involves its furan oxygen and the hydroxyl of the opposite α1Ser138 (inter-subunit interaction). The pyranose ring also makes inter-subunit hydrophobic interactions with β2Pro36 and β2Trp37. Like the α2-subunit, there are also two alternate conformers of MMA-509 bound at the α1-subunit α1Val1 nitrogen with similar interactions as described above for the α2-subunit conformers. The pyranose ring of one of conformers from the α1-subunit makes close hydrophobic interactions with the pyranose ring of its counterpart from the α2-subunit. MMA-509 makes similar intra- and inter-subunit hydrogen-bond as 5-HMF and, importantly, demonstrates that additional hydrophobic interactions are missing in 5-HMF, which may explain the compound's significant potency over 5-HMF.

In contrast to MMA-509, MMA-503 compounds bind to each α-subunit in a single conformation (FIG. 4B). Like MMA-509, the electron density at the α2-subunit is better resolved than at the α1-subunit. In addition to the Schiff-base interaction with α2Val1 nitrogen, MMA-503 also makes additional interactions with the protein, including an inter-subunit hydrogen-bond between its furan oxygen and the hydroxyl of α1Ser138, inter-subunit hydrogen-bond between its imidazole nitrogen and the hydroxyl of α1Ser138, inter-subunit hydrophobic interactions between the imidazole ring and β2Trp37. Unlike MMA-509, there are no apparent interactions between the two bound MMA-503 compounds. This study demonstrated that MMA-503 forms fewer interactions with the protein when compared with MMA-509 and this may explain its relatively weaker potency compared with MMA-509. Nonetheless, the additional hydrophobic interactions by MMA-503 may explain its significant potency over 5-HMF.

In further contrast to MMA-509 and MMA-503, only the α2-subunit of the MMA-505 complex structure showed good electron density for the bound compound, resulting in modeling only one MMA-505 at the α-cleft at the α2-subunit (FIG. 4C). The density of the second bound compound at the α1-subunit was very weak to allow for proper fitting and refinement. Expectedly, MMA505 also forms a Schiff-base interaction with α2Val1 nitrogen. In addition, both the furan oxygen and the nitrile nitrogen atoms make inter-subunit hydrogen-bond interactions with the hydroxyl of α1Ser138. Interestingly, the nitrile has rotated into an alternate conformation to make several water-mediated hydrogen bond interactions with the protein. Unlike MMA-509 and MMA-503, there are no hydrophobic interactions with the protein, which explains its weaker biological effect compared to the MMA-503 and MMA-509.

The final Rafctor/Rfree of MMA509, MMA505, and MMA503 are 16.84/22.80, 16.55/20.75, and 16.20/21.50, respectively. Detailed crystallographic data collected for all three structures are shown in Table 4.

TABLE 4

Crystallographic data and refinement statistics for MMA compounds in complex with Hb.

| Compound | MMA509 | MMA505 | MMA503 |
|---|---|---|---|
| Data collection statistics | | | |
| Space group | $P2_12_12_1$ | $P2_12_12_1$ | $P2_12_12_1$ |
| Unit-cell a, b, c (Å) | 62.8, 83.7, 105.24 | 62.65, 82.92, 104.91 | 62.61, 83.12, 105.12 |
| Resolution (Å) | 28.3-2.0 (2.072-2.0) | 28.65-2.00 (2.07-2.00) | 28.22-2.00 (2.07-2.00) |

TABLE 4-continued

Crystallographic data and refinement statistics for
MMA compounds in complex with Hb.

| Compound | MMA509 | MMA505 | MMA503 |
|---|---|---|---|
| Unique reflections | 38131 (3752) | 37589 (3689) | 37734 (3701) |
| Redundancy | 7.4 | 5.8 | 6.3 |
| Completeness (%) | 99.8 (99.9) | 99.9 (99.9) | 99.9 (100) |
| Average I/σ(I) | 27.9 (4.89) | 28.7 (5.9) | 35.33 (9.06) |
| $R_{merge}$ (%)$^a$ | 6.5 (34.9) | 2.9 (18.0) | 4.5 (19.8) |
| Refinement Statistics | | | |
| Resolution (Å) | 28.3-2.00 | 28.65-2.00 | 28.22-2.00 |
| No. of reflections | 38131 | 37589 | 37734 |
| $R_{work}$ (%) | 16.84 | 16.55 | 16.20 |
| $R_{free}$ (%)$^b$ | 22.60 | 20.75 | 21.50 |
| R.m.s.d. bonds (Å) | 0.012 | 0.008 | 0.013 |
| R.m.s.d. angles (°) | 1.37 | 1.19 | 1.39 |
| Dihedral angles | | | |
| Most favored (%) | 98.06 | 98.59 | 98.06 |
| Allowed (%) | 1.94 | 1.24 | 1.59 |
| Average B (Å$^2$)/atoms | | | |
| All atoms | 21.45 | 22.96 | 21.01 |
| Protein | 20.26 | 21.68 | 19.81 |
| Ligand | 18.98 | 19.01 | 19.26 |
| Water | 29.04 | 31.14 | 28.34 |

$^a R_{merge} = \Sigma_{hkl}\Sigma_i |I_i(hkl) - <I(hkl)>| \Sigma_{hkl}\Sigma_i I_i(hkl)$.
$^b R_{free}$ was calculated from 5% randomly selected reflection for cross-validation.
All other measured reflections were used during refinement.

The crystallographic study provides insight into the activities of the MMA compounds. MMA-509 makes by far the greatest number of interactions with the protein, followed by MMA-503, and lastly MMA-505. The number of interactions corresponds with the observed trend in their functional/biological activities. Without being bound by theory, the superior pharmacologic activity of MMA-509 or MMA-503 when compared to 5-HMF could in part be due to hydrophobic interactions as well as the hydrogen-bond interactions, the former absent in 5-HMF. Like MMA-503 or MMA-509 or MMA-505, both MMA-502 and MMA-504 are also capable of making hydrogen-bond interactions with the protein, although it is most likely that the hydroxyl of MMA-504, which is far removed from the furan ring, might not be in the right position and/or orientation to make such hydrogen-bond interactions, explaining its comparatively weak activity.

Example 3—In Vitro Time-Dependent HB Oxygen Equilibrium Studies Using Normal Whole Blood The time-dependent effect of the MMA compounds and positive control 5-HMF on Hb oxygen affinity was studied using normal blood following previous procedure.[15] Briefly, normal blood samples (hematocrit 20%) were incubated with the compounds at 37° C. for 24 h. Aliquots were taken at various time points and incubated in IL 237 tonometers (Instrumentation Laboratories, Inc. Lexington, Mass.) for 10 minutes at 37° C., and allowed to equilibrate at oxygen tensions 6, 20, and 40 mmHg. The samples were then aspirated into an ABL 700 Automated Blood Gas Analyzer (Radiometer) to determine the pH, partial pressure of $CO_2$ ($pCO_2$), partial pressure of oxygen ($pO_2$), and Hb oxygen saturation values ($SO_2$). The measured values of $pO_2$ (mmHg) and $SO_2$ at each $pO_2$ value were then subjected to a non-linear regression analysis using the program Scientist (Micromath, Salt Lake City, Utah) to estimate $P_{50}$ as previously reported.[28]

Results

MMA compounds showed quick onset and relatively short duration of action. Unlike Voxelotor, most aromatic aldehydes including 5-HMF are highly susceptible to oxidative and/or reductive metabolism to the inactive carboxylic and/or alcohol analogs, respectively.[22-24] 5-HMF has a short half-life and poor oral bioavailability due to this metabolic instability, which in part prevented its development for chronic use. Nonetheless, this metabolic instability could be advantageous for parenteral formulation for acute use. We tested the three compounds, MMA-503, MMA-505 and MMA-509, for their time-dependent (0, 1, 1.5, 3, 6 and 8 hrs) effect on Hb oxygen affinity using normal whole blood as previously reported.[13-15] Briefly, blood samples (hematocrit 20%) were incubated with the compounds at 37° C. for 24 h, and aliquots were taken at the various time points and used to determine the $PO_2$ and $SO_2$ using ABL 800 Automated Blood Gas Analyzer (Radiometer), and to estimate $P_{50}$ as previously reported.[10]

Figure 5:
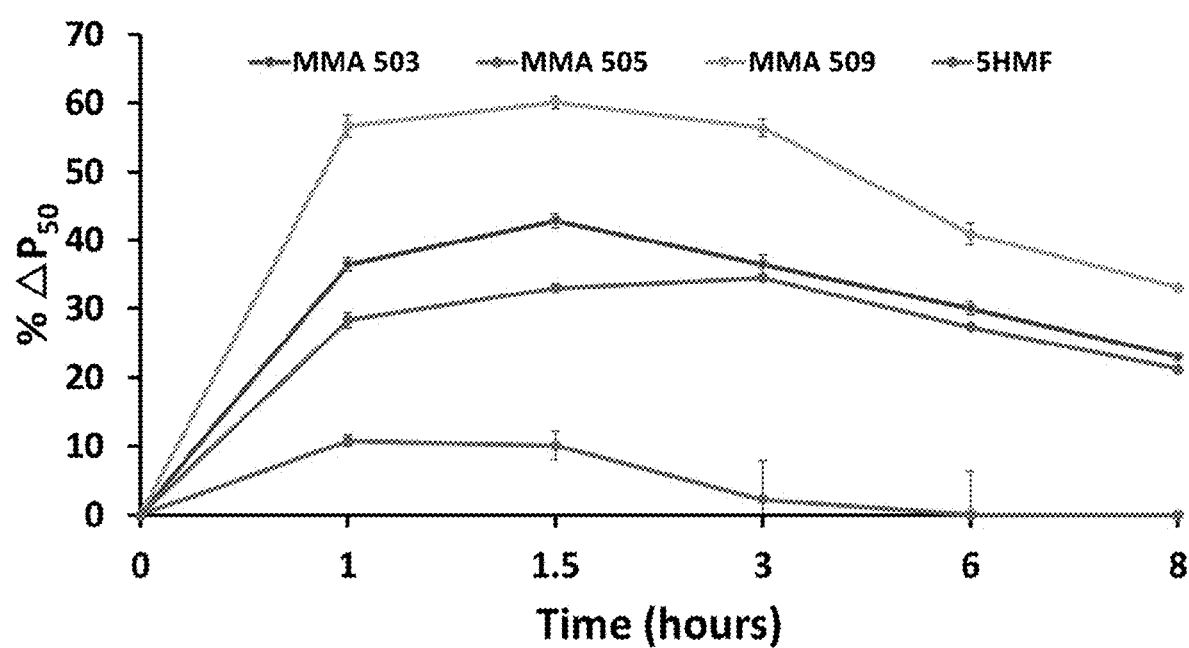
FIG. 5 shows a time-dependent P$_{50}$-shift of HbA in normal blood (20% hematocrit) incubated with 2 mM of test compounds (MMA-503, MMA-505 or MMA-509) or control compound (5-HMF).

The observed $P_{50}$ shifts values in %$P_{50}$ shifts were plotted as function of time in units of hours, as shown in FIG. 5. The time-dependent study gives indication of the compounds' duration of action since whole blood contains enzymes that are known to metabolize the aldehyde moiety into the inactive alcohol or acid. The study confirmed the trend in the biological potencies observed with SS blood. As expected, MMA-509 showed the most potent effect at all time points (60% at 1.5 hours), followed by MMA-503 (43% at 1.5 hours), then 5-HMF (35% at 3 hours), and lastly MMA-505 (11% at 1hour). Nonetheless, all the compounds, including 5-HMF, started to decline in their biological effect after 3 hours, with MMA-505 completely losing activity after 3 hours.

Example 4—Toxicity: MMA-509 Showed No CYP Inhibition

The MMA-509 compound, in addition to the positive control 5-HMF, was studied for inhibitory potential of seven major drug metabolizing human cytochrome P450 (CYP) enzymes (CYP1A2, CYP2C8, CYP2C9, CYP2C19, CYP2D6, CYP3A4, CYP2B6) using pooled human liver microsomes as previously published.[25,26] The probe substrates include tacrine (CYP1A2), amodiaquine (CYP2C8), tolbutamide (CYP2C9), mephenytoin (CYP2C19), dextromethorphan (CYP2D6), midazolam (CYP3A4), testosterone (CYP3A4), and bupropion (CYP2B6). The following selective CYP inhibitors, naphthoflavone (CYP1A2), quercetine (CYP2C8), sulfaphenazole (CYP2C9), ticlopidine (CYP2C19), quinidine (CYP2D6), ketoconazole (CYP3A4), and ticlopidine (CYP2B6) were used as positive controls. The optimized reaction mixtures (200 µL) contained a final concentration of 0.2-0.5 mg/mL pooled human liver microsomes, 2 mM NADPH in 100 mM potassium phosphate, pH 7.4 buffer with 5 mM MgCl2, and MMA509 or 5-HMF concentration of 0.1 to 100 µM. The assays were performed in duplicate in 96-well plates at 37° C. for 10-60 minutes. The reaction was terminated with addition of methanol, followed by incubation at 4° C. for 10 min and centrifuged at 4° C. for 10 min. The effect of test compounds on formation of the respective probe substrate metabolites were determined using LC-MS/MS, and used to calculate $IC_{50}$ value, which is the test compound concentration that resulted in 50% inhibition.

Results

The probe substrates for the CYP enzymes, as well as the selective CYP inhibitors are provided in Table 5. Like the natural product 5-HMF, MMA-509 showed no inhibition of any of the liver CYP isozymes, suggestive of a potential low liability for toxic effect.

TABLE 5

In Vitro CYP Inhibition with MMA-509 and 5-HMF

| | | | $IC_{50}$ (µM) | |
|---|---|---|---|---|
| Enzyme | Substrate | Control Inhibitor | MMA-509 | 5HMF |
| CYP1A2 | Tacrine | α-Naphthoflavone (0.007) | >100 | >100 |
| CYP2C8 | Amodiaquine | Quercetin (1.90) | >100 | >100 |
| CYP2C9 | Tolbutamide | Sulfaphenazole (0.098) | >100 | >100 |
| CYP2C19 | Mephentoin | Ticlopidine (0.965) | >100 | >100 |
| CYP2D6 | Dextro-methorphan | Quinidine (0.061) | >100 | >100 |
| CYP3A4 | Midazolam | Ketoconazole (0.024) | >100 | >100 |
| CYP3A4 | Testosterone | Ketoconazole (0.023) | >100 | >100 |
| CYP2B6 | Bupropion | Ticlopidine (0.262) | >100 | >100 |

CONCLUSIONS

Aromatic aldehydes have for several years been studied for their potential to treat sickle cell disease by preventing hypoxia-induced sickle Hb polymerization and the concomitant RBC sickling. Voxelotor is one such compound and has been approved for the treatment of the disease. Nonetheless, Voxelotor's hydrophobic nature and significantly long-half-life makes it inappropriate for parenteral use and/or for achieving quick therapeutic steady-state drug level to treat acute symptoms, which sometimes is life-threatening. The claimed 5-HMF derivatives are aromatic aldehyde that target αVal1 amines of Hb for their antisickling mechanism of action. In contrast, U.S. Pat. No. 10,836,729 claims 5-HMF derivatives that are Michael acceptors, which target βHis93 for their antisickling mechanism of action. The present invention takes advantage of 5-HMF's non-toxic profile, solubility and relatively short half-life to look for analogs that not only retain its optimal physicochemical, solubility, and non-toxic profile but also with significantly improved biological activities. Two such compounds, MMA-509 and MMA-503 have been identified as having properties that are useful for the method of the invention. These compounds exhibit at least 3.5-fold more potent antisickling activity than 5-HMF. Thus, MMA-509 and MMA-503 represent a class of compounds with potential therapeutic application for SCD, especially for parenteral loading dose to facilitate rapid loading to steady state, and subsequently the therapeutic level in red blood cells, and thus deliver fast treatment that would be critical to prevent or treat acute crises or acute anemia. While less potent than some of the MMA compounds tested, MMA-505 nonetheless has solubility properties that may render it more efficacious for parenteral delivery than 5-HMF or other aromatic aldehydes, such as Voxelotor, upon further testing and validation in vivo.

REFERENCES

1. Piel et al. *PLoS Medicine* 2013, doi:10.1371/journal.pmed.1001484.
2. Hassell, K. L. *Am J Preventive Medicine* 2010.
3. Kauf et al. *Am J Hematology* 2009, doi:10.1002/ajh.21408.
4. Safo et al. *Hematol. Oncol Clin North Am* 2014, 28, 217-231, doi:10.1016/j.hoc.2013.11.001.
5. Aliyu et al. *Am J Hematol.* 2008, 83, 485-490, doi: 10.1002/ajh.21162.
6. Akinsheye et al. *J Cell Physiol.* 2010, 224, 620-625, doi:10.1002/jcp.22195.
7. De Franceschi, L. *Mediterr J Hematol Infect Dis* 2009,1, e2009024, doi:10.4084/MJHID.2009.024.
8. Belcher et al. *Blood* 2003, 101, 3953-3959, doi:10.1182/blood-2002-10-3313.
9. Piel et al. *N Engl J Med.* 2017, 377, 305, doi:10.1056/NEJMc1706325.
10. Safo et al. *J Med Chem.* 2004, 47, 4665-4676, doi: 10.1021/jm0498001.
11. Abdulmalik et al. *Br J Haematol.* 2005, 128, 552-561, doi:10.1111/ j.1365-2141.2004.05332.x.
12. Abdulmalik et al. *Acta Crystallogr D Biol Crystallogr* 2011, D67, 920-928.
13. Deshpande et al. *Acta crystallographica. Section D, Structural biology* 2018, 74, 956-964, doi:10.1107/S2059798318009919.
14. Pagare et al. *Bioorg Med Chem.* 2018, 26, 2530-2538, doi:10.1016/j.bmc.2018.04.015.
15. Xu et al. *Mol Pharm.* 2017,14, 3499-3511, doi:10.1021/acs.molpharmaceut.7b00553.
16. Metcalf et al. *ACS Med Chem Lett* 2017, 8, 321-326, doi:10.1021/acsmedchemlett.6b00491.
17. Oksenberg et al. *Br J Haematol.* 2016, 175, 141-153, doi:10.1111/bjh.14214.
18. Dufu et al. *Am J Physiol Heart Circ. Physiol.* 2017, 313, H381-H391, doi:10.1152/ajpheart.00772.2016.
19. Vichinsky et al. *New Engl J Med* 2019, doi:10.1056/NEJMoa1903212.
20. Abdulmalik et al. *Scientific Reports* 2020, 10, doi: 10.1038/s41598-020-77171-2.
21. Pagare et al. *J Medicinal Chem.* 2020, doi:10.1021/acs.jmedchem.0c01287.
22. Godfrey et al. *J Toxicol Environ Health Part A* 1999, 57, 199-210.
23. Yoshida et al. *Eur J Biochem.* 1998, 251, 549-557, doi:10.1046/ j.1432-1327.1998.2510549.x.
24. Vasiliou et al. *Chem Biol Interact.* 2000, 129, 1-19.

25. Metcalf et al. *ACS Med Chem Lett.* 2017, 8, 321-326, doi:10.1021/acsmedchemlett.6b00491.
26. Obach et al. *J Pharmacol Exp Ther.* 2006, 316, 336-348, doi:10.1124/jpet.105.093229.
27. Deshpande et al. *Acta Crystallogr D Struct Biol* 2018, 74, 956-964, doi:10.1107/S2059798318009919.
28. Safo et al. *J Med Chem.* 2004, 47, 4665-4676, doi: 10.1021/jm0498001.
29. Adams et al. *Methods* 2011, 55, 94-106, doi:10.1016/j.ymeth.2011.07.005.
30. Echolset al. *J Appl Crystallogr* 2012, 45, 581-586, doi:10.1107/S0021889812017293.
31. Brünger et al. *Acta Crystallogr. D Biol. Crystallogr.* 1998, 54, 905-921.

While the invention has been described in terms of its several exemplary embodiments, those skilled in the art will recognize that the invention can be practiced with modification within the spirit and scope of the appended claims. Accordingly, the present invention should not be limited to the embodiments as described above but should further include all modifications and equivalents thereof within the spirit and scope of the description provided herein.

We claim:

1. A method of inhibiting or reversing sickling of red blood cells comprising hemoglobin S (HbS), comprising the steps of
contacting red blood cells with a therapeutically effective amount of a furfural derivative or analog selected from the group consisting of

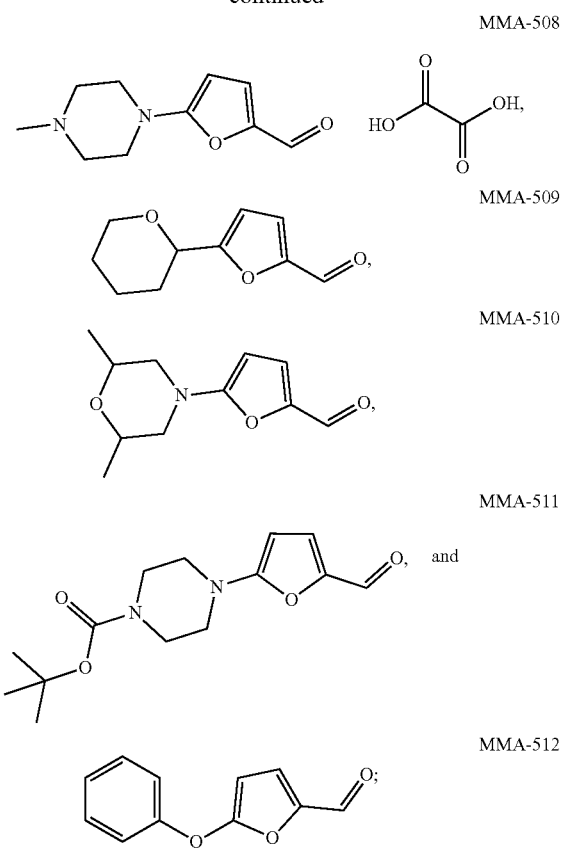

wherein the therapeutically effective amount is a parenteral loading dose sufficient to reach equilibrium of hemoglobin oxygen affinity in the red blood cells and inhibit or reverse polymerization of HbS.

2. The method of claim 1, wherein equilibrium of the hemoglobin oxygen affinity is reached within 30 to 90 minutes.

3. The method of claim 1, wherein equilibrium of the hemoglobin oxygen affinity is reached within 60 minutes.

4. The method of claim 1, wherein the hemoglobin oxygen affinity reaching equilibrium is that of HbS.

* * * * *